(12) United States Patent
Lee et al.

(10) Patent No.: US 10,133,851 B2
(45) Date of Patent: Nov. 20, 2018

(54) MOLECULAR ORBITAL LIBRARY HAVING EXCLUSIVE MOLECULAR ORBITAL DISTRIBUTION, MOLECULAR ORBITAL DISTRIBUTION REGION EVALUATION METHOD USING SAME, AND SYSTEM USING SAME

(71) Applicant: LG CHEM, LTD., Seoul (KR)

(72) Inventors: Seungyup Lee, Daejeon (KR); Hyesung Cho, Daejeon (KR)

(73) Assignee: LG CHEM, LTD., Seoul (KR)

( * ) Notice: Subject to any disclaimer, the term of this patent is extended or adjusted under 35 U.S.C. 154(b) by 319 days.

(21) Appl. No.: 14/899,704

(22) PCT Filed: Jul. 16, 2014

(86) PCT No.: PCT/KR2014/006423
§ 371 (c)(1),
(2) Date: Dec. 18, 2015

(87) PCT Pub. No.: WO2015/009046
PCT Pub. Date: Jan. 22, 2015

(65) Prior Publication Data
US 2016/0140325 A1   May 19, 2016

(30) Foreign Application Priority Data

Jul. 18, 2013 (KR) .................. 10-2013-0084624

(51) Int. Cl.
*G06F 19/00* (2018.01)
*G06F 17/10* (2006.01)

(52) U.S. Cl.
CPC ............ *G06F 19/701* (2013.01); *G06F 17/10* (2013.01)

(58) Field of Classification Search
CPC ...... G06F 19/701; G06F 17/10; G06F 19/704; A01K 67/033
See application file for complete search history.

(56) References Cited

U.S. PATENT DOCUMENTS

| 7,945,396 B2 | 5/2011 | Fujitani et al. | |
| 2004/0260529 A1* | 12/2004 | Takada | G06F 17/10 |
| | | | 703/21 |

(Continued)

FOREIGN PATENT DOCUMENTS

| EP | 1 443 415 A1 | 8/2004 |
| JP | 2011-173821 A | 9/2011 |

OTHER PUBLICATIONS

J.Phys., "Analysis of Electron Delocalization in Aromatic Systems: Individual Molecular Orbital Contributions to Para-Delocalization Indexes," Chem. A., 2006, 110, pp. 11569-11574.

*Primary Examiner* — Changhyun Yi
(74) *Attorney, Agent, or Firm* — Dentons US LLP

(57) ABSTRACT

Disclosed herein are a method for constructing an extended R-MO library with mutually exclusive molecular orbital distribution, calculation method of molecular orbital distributing region and a system using the same. The molecular orbital distributing region estimation method using a molecular orbital library with a mutually exclusive orbital distribution can accurately molecular orbital distributing regions in a quantitative manner by means of an extended R-MO library that expresses intrinsic molecular distributing region properties in various patterns. In addition, the coverage of the quantitative molecular orbital distribution estimation method can be extended to the systemic utilization of molecular orbital information in developing materials.

3 Claims, 11 Drawing Sheets

(56) References Cited

U.S. PATENT DOCUMENTS

| | | | |
|---|---|---|---|
| 2007/0043545 A1* | 2/2007 | Yonezawa | G06F 19/701 703/11 |
| 2008/0059549 A1* | 3/2008 | Aoki | G06F 19/701 708/401 |
| 2009/0182514 A1* | 7/2009 | Fujitani | G06F 19/701 702/27 |
| 2013/0041638 A1* | 2/2013 | Nagahori | G06F 19/704 703/2 |

* cited by examiner

MOLECULAR ORBITAL LIBRARY HAVING EXCLUSIVE MOLECULAR ORBITAL DISTRIBUTION, MOLECULAR ORBITAL DISTRIBUTION REGION EVALUATION METHOD USING SAME, AND SYSTEM USING SAME

This application is a National Stage Entry of International Application No. PCT/KR2014/006423, filed on Jul. 16, 2014, and claims the benefit of and priority to Korean Application No. 10-2013-0084624, filed on Jul. 18, 2013, all of which are hereby incorporated by reference in their entirety for all purposes as if fully set forth herein.

TECHNICAL FIELD

The present invention relates to a method for estimating a molecular orbital distributing region using a molecular orbital library with a mutually exclusive molecular orbital distribution, and a system using the same. More particularly, the present invention relates to a novel analysis method by which molecular orbital distributions can be quantitatively compared, a calculation method of a molecular orbital distribution region using the same, and a system using the same.

BACKGROUND ART

Because intrinsic electrochemical properties of materials are greatly influenced by electron transfer and distribution therein, it is very important to simulate the behavior of an electron in a molecule in developing a material. The behavior of an electron is expressed as the probability of finding an electron in any specific region in a molecular. A molecular orbital is introduced as a concept to simulate the behavior of an electron. A molecular orbital, which accounts for the distribution of an electron in a specific region in a molecular structure as a probability concept, cannot be obtained experimentally, but can be constructed by the Schrödinger equation using quantum mechanics.

The molecular orbital distribution that has been quantum-mechanically computed thus far is regarded as a qualitative measurement in which 3- or 2-dimensional diagrams created through a contour plot are used for visual comparison, for example, as described in "Analysis of Electron Delocalization in Aromatic Systems: Individual Molecular Orbital Contributions to Para-Delocalization Indexes (PDI)". FIG. 1 is a diagram showing the molecular orbital distribution of NPB (N,N'-Di[(1-naphthyl)-N,N'-diphenyl]-1,1'-(biphenyl)-4,4'-diamine), which is used in an OLED film, in terms of Neutral/HOMO. To depict FIG. 1, Materials Visualizer of the program Materials Studio for simulating and modeling molecular orbitals was used. In the diagram, the molecular orbital distribution is expressed as a region in which an electron is likely to exist (yellow/green regions). FIG. 1 shows a generally even molecular orbital distribution over the entire molecule.

As is perceived in this case, however, the qualitative measurement through visualization does not provide an accurate criterion of analysis, so that even the same molecular orbital distribution may be analyzed differently. For FIG. 1, by way of example, there may be different estimation results: (1) the molecular orbital is highly evenly distributed because the molecular orbital is distributed over the entire molecule, or (2) the molecular orbital is fairly distributed because the distribution is poor in opposite ends of the naphthalene moieties. The problem with this qualitative measurement is more evident when two molecular orbital distributions, rather than one molecule, are compared to each other. In many materials development cases, electrochemical properties are estimated by comparing the distribution of molecular orbital A with that of molecular orbital B. Since the qualitative comparison through visualization may result in greatly different estimation data depending on the criterion, estimation of two or more molecular orbital distributions is more prone to being inaccurate than that of one molecular orbital distribution. This problem does not arise only upon the comparison of molecular orbital distributions, but is one of the most fundamental limits for all qualitative approaches. Given an effective, accurate and reliable measurement approach to the molecular orbital distribution, which has been estimated only qualitatively thus far, materials development can be more effectively achieved with reference to properties determined by the molecular orbital distribution as well as the fundamental properties determined by electron transfer, such as electron affinity.

In this regard, Japanese Patent Application Unexamined Publication No. 2011-173821 discloses a novel method for predicting the activity of a new chemical material using an index of reactivity of a molecule, computed on the basis of quantum chemistry calculation in consideration of a reactive molecular orbital as well as a frontier orbital. However, this conventional method is limitedly applied to the quantitative comparison of molecular orbital distributions between two molecules.

To overcome the limitation of conventional qualitative methods, the present inventors developed the novel method MOD-Dscore by which molecular orbital distribution profiles can be quantitatively estimated. Configured to have a value between 0.0 and 1.0, the system established by the MOD-Dscore method further approaches to 1.0 for a more identical orbital distribution between two molecules, and is farther away from 1.0 for greater difference in molecular orbital distribution between two molecules. MOD-Dscore allows for the expression of a difference in molecular orbital distribution between two molecules as a digitized value, thereby accurately estimating molecular orbital distributions in a quantitative manner.

For instance, assume that molecules A1, A2, and A3 are calculated to have MOD-Dscore values of 0.995, 0.875, and 0.893, respectively, with regard to molecule A over the entire structure of which a molecular orbital is evenly distributed. The molecular orbital distribution of A1 is regarded as being similar to that of A because its MOD-Dscore value is 0.995, which approximates to 1.0 whereas A2 and A3 are estimated to be different in molecular orbital distribution from A because their MOD-Dscore values are significantly smaller than 1.0. As such, MOD-Dscore computation can reveal that the molecular orbitals are not evenly distributed over the entire molecules of A2 and A3; however, it cannot explain the regions where the molecular orbitals of A2 and A3 are localized, which makes A2 and A3 different in molecular orbital properties from A. There is now a need for a novel approach to assessing a region where a molecular orbital is localized. In this context, first, the present inventors construct a region specific-molecular orbital library (R-MO library), which can be used as a reference in assessing molecular orbital distributing regions. Constructed with molecular orbital distributions of materials having specific structure regions, the R-MO library can be used as a reference in estimating molecular orbital distributing regions, and there is also a need for extending the R-MO library.

DISCLOSURE

Technical Problem

It is an object of the present invention to provide a method for estimating a molecular orbital distributing region by which the molecular orbital distributing region is quantitatively estimated using an R-MO library and an extended R-MO library, both constructed with a variety of patterns of representative molecular orbital distributing regions.

Technical Solution

In order to accomplish the above object, the present invention provides a method for constructing an extended R-MO library (Extended-Region specific-Molecular Orbital Library), comprising:

a) selecting A(1) belonging to a group of materials that have a specific-type molecular orbital and then selecting A(2) if it has a MOD-Dscore value of p or less, as obtained by conducting the following steps i) to iii), with regard to A(1):

i) selecting two molecular orbitals to be compared for molecular orbital distributions and computing molecular orbital distributions by quantum chemistry calculation, ii) calculating structural properties of each molecular orbital by means of an RDM (radially discrete mesh) calculation method, followed by matching with the molecular orbital distributions computed in step i) to obtain molecular orbital distributions according to the structural properties, and iii) calculating MOD-Dscore (Molecular Orbital Distribution-Deviation Score) of the following equation 2 by use of the molecular orbital distribution according to structural property obtained in step ii);

b) incorporating A (1) and A(2), determined in a), as constituents into an R-MO library (Region specific-Molecular Orbital Library);

c) calculating respective MOD-Dscore values of A(3), which is selected from the group of the materials, with regard to plural materials already incorporated into the R-MO library (Region specific-Molecular Orbital Library), and incorporating A(3) as a constituent A(m) into the R-MO library (Region specific-Molecular Orbital Library) if the MOD-Dscore values are calculated to have a maximum of q or less and a minimum of r or less;

d) repeating step c) for all materials of the group to determine whether individual materials can be included within the R-MO library and thus to find the constituents A(m) of the R-MO library;

e) calculating MOD-Dscore values of AX(1), one of the candidate materials AX(k) that are not incorporated into the R-MO library, with regard to all the constituents A(m) of the R-MO library obtained in step d), and incorporating AX(1) as an extended constituent Am(k') into the extended R-MO library (Extended-Region specific-Molecular Orbital Library) of the constituent A(m) if the MOD-Dscore values have a maximum of p' or greater; and f) repeating step e) for all candidate materials AX(k) to determine whether individual candidate materials can be included within the extended R-MO library, wherein $0.7 \leq p \leq 0.8$, $0.85 \leq q \leq 0.95$, $0.65 \leq r \leq 0.75$, and $0.90 \leq p' < 1.0$, MOD-Dscore=1.0−TPD  (Equation 2)

(wherein TPD is Equation 3.)

$$TPD = \frac{1}{N}\sum_{k=1}^{N} |Prof(A_k) - Prof(B_k)| \quad \text{(Equation 3)}$$

(wherein $Prof(A_k)$ and $Prof(B_k)$ are respective molecular orbital values belonging to RDM(k), and N is a total number of RDM.)

Also, the present invention provides a system for constructing an extended R-MO library (Extended-Region specific-Molecular Orbital Library), comprising:

a) an initial setting module for selecting A(1) belonging to a group of materials that have a specific-type molecular orbital and then selecting A(2) if it has a MOD-Dscore value of p or less, as obtained by conducting the following steps i) to iii), with regard to A(1), and for incorporating A (1) and A(2) as constituents into an R-MO library (Region specific-Molecular Orbital Library):

i) selecting two molecular orbitals to be compared for molecular orbital distributions and computing molecular orbital distributions by quantum chemistry calculation, ii) calculating structural properties of each molecular orbital by means of an RDM (radially discrete mesh) calculation method, followed by matching with the molecular orbital distributions computed in step i) to obtain molecular orbital distributions according to the structural properties, and iii) calculating MOD-Dscore (Molecular Orbital Distribution-Deviation Score) of the following equation 2 by use of the molecular orbital distribution according to structural property obtained in step ii);

b) a constituent-determining module for calculating respective MOD-Dscore values of A(3), which is selected from the group of the materials, with regard to plural materials already incorporated into the R-MO library (Region specific-Molecular Orbital Library), for incorporating A(3) as a constituent A(m) into the R-MO library (Region specific-Molecular Orbital Library) if the MOD-Dscore values are calculated to have a maximum of q or less and a minimum of r or less, and for repeating the above procedure for all materials of the group to determine whether individual materials can be included within the R-MO library and thus to find the constituents A(m) of the R-MO library;

c) an extended material-determining module for calculating MOD-Dscore values of AX(1), one of the candidate materials AX(k) that are not incorporated into the R-MO library, with regard to all the constituents A(m) of the R-MO library, for incorporating AX(1) as an extended constituent Am(k') into the extended R-MO library (Extended-Region specific-Molecular Orbital Library) of the constituent A(m) if the MOD-Dscore values have a maximum of p' or greater; and for repeating the above procedure for all candidate materials AX(k) to determine whether individual candidate materials can be included within the extended R-MO library, wherein $0.7 \leq p \leq 0.8$, $0.85 \leq q \leq 0.95$, $0.65 \leq r \leq 0.75$, and $0.90 \leq p' < 1.0$, MOD-Dscore=1.0−TPD  (Equation 2)

(wherein TPD is Equation 3)

$$TPD = \frac{1}{N}\sum_{k=1}^{N} |Prof(A_k) - Prof(B_k)| \quad \text{(Equation 3)}$$

(wherein Prof($A_k$) and Prof($B_k$) are respective molecular orbital values belonging to RDM(k), and N is a total number of RDM)

Advantageous Effects

As described hitherto, the molecular orbital distributing region estimation method using a molecular orbital library with a mutually exclusive orbital distribution in accordance with the present invention can accurately estimate molecular orbital distributing regions in a quantitative manner by means of an extended R-MO library that expresses intrinsic molecular distributing region properties in various patterns. In addition, the coverage of the quantitative molecular orbital distribution estimation method can be extended to the systemic utilization of molecular orbital information in developing materials.

BEST MODE

Figure 1:
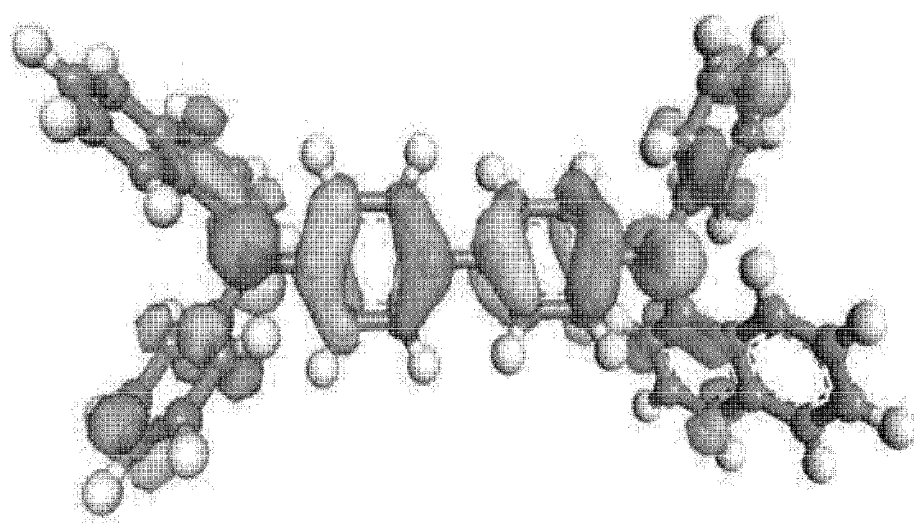
FIG. 1 is a diagram of the structure and molecular orbital distribution of NPB.

On the basis of the R-MO library constructed for use as a reference, the present inventors developed an extended R-MO library, which can explain various patterns of molecular orbital distributing region properties. The extended R-MO library includes constituents of the R-MO library that are responsible for specific molecular orbital distributing region properties, and extended materials that account for various patterns of the distributing region properties of each constituent. In addition, the present inventors developed a method for quantitatively estimating molecular orbital distributing region, termed MODREM (Molecular Orbital Distributing Region Estimation Method), using the extended R-MO library. Capable of extending the quantitative estimation of molecular orbital distributions to molecular orbital distributing regions, the extended R-MO library, and MODREM using the same in accordance with the present invention are expected to afford for the systemic utilization of molecular orbital information. Below, a detailed description will be given of the extended R-MO library and the quantitative estimation method of molecular orbital distributions using the same in accordance with the present invention.

In accordance with an aspect thereof, the present invention addresses a method for constructing an extended R-MO library (Extended-Region specific-Molecular Orbital Library), comprising:

a) selecting A(1) belonging to a group of materials that have a specific-type molecular orbital and then selecting A(2) if it has a MOD-Dscore value of p or less, as obtained by conducting the following steps i) to iii), with regard to A(1):

i) selecting two molecular orbitals to be compared for molecular orbital distributions and computing molecular orbital distributions by quantum chemistry calculation, ii) calculating structural properties of each molecular orbital by means of an RDM (radially discrete mesh) calculation method, followed by matching with the molecular orbital distributions computed in step i) to obtain molecular orbital distributions according to the structural properties, and iii) calculating MOD-Dscore (Molecular Orbital Distribution-Deviation Score) of the following equation 2 by use of the molecular orbital distribution according to structural property obtained in step ii);

b) incorporating A(1) and A(2), determined in a), as constituents A(m) into an R-MO library (Region specific-Molecular Orbital Library);

c) calculating respective MOD-Dscore values of A(3), a member selected from the group of the materials, with regard to plural materials already incorporated into the R-MO library (Region specific-Molecular Orbital Library), and incorporating A(3) as a constituent A(m) into the R-MO library (Region specific-Molecular Orbital Library) if the MOD-Dscore values are calculated to have a maximum of q or less and a minimum of r or less;

d) repeating step c) for all materials of the group to determine whether individual materials can be included within the R-MO library and thus to find the constituents A(m) of the R-MO library;

e) calculating MOD-Dscore values of AX(1), one of the candidate materials AX(k) that are not incorporated into the R-MO library, with regard to all the constituents A(m) of the R-MO library obtained in step d), and incorporating AX(1) as an extended constituent Am(k') into the extended R-MO library (Extended-Region specific-Molecular Orbital Library) of the constituent A(m) if the MOD-Dscore values have a maximum of p' or greater; and f) repeating step e) for all candidate materials AX(k) to determine whether individual candidate materials can be included within the extended R-MO library, wherein $0.7 \leq p \leq 0.8$, $0.85 \leq q \leq 0.95$, $0.65 \leq r \leq 0.75$, and $0.90 \leq p' < 1.0$, $$\text{MOD-}D\text{score} = 1.0 - TPD \quad \text{(Equation 2)}$$

(wherein TPD is Equation 3.)

$$TPD = \frac{1}{N} \sum_{k=1}^{N} |Prof(A_k) - Prof(B_k)| \quad \text{(Equation 3)}$$

(wherein Prof(Ak) and Prof(Bk) are respective molecular orbital values belonging to RDM(k), and N is a total number of RDM.)

Herein, the present inventors termed extended R-MO library "Ext-R-MO library (Extended-Region specific-Molecular Orbital Library)". The method for constructing an Ext-R-MO library is a method by which molecular orbital distributing regions can be accurately estimated in a quantitative manner using an extended R-MO library representative of various patterns of specific molecular orbital distributing region properties. Hereinafter, the method for constructing an Ext-R-MO library is explained in detail.

In step a) of the method for constructing an Ext-R-MO library, A(1) belonging to a group of materials that have a specific-type molecular orbital is selected and then A (2) is selected if it has a MOD-Dscore value of p or less, as obtained by conducting the following steps i) to iii), with regard to A(1).

The MOD-Dscore value used in the present invention can be obtained by i) selecting two molecular orbitals to be compared for molecular orbital distributions and computing molecular orbital distributions by quantum chemistry calculation; ii) calculating structural properties of each molecular orbital by means of an RDM (radially discrete mesh) calculation method, followed by matching with the molecular orbital distributions computed in step i) to obtain molecular orbital distributions according to the structural properties, and iii) calculating MOD-Dscore (Molecular Orbital Distribution-Deviation Score) of the following equation 2 by use of the molecular orbital distribution according to structural properties obtained in step ii);

$$\text{MOD-}D\text{score} = 1.0 - \text{TPD} \quad \text{(Equation 2)}$$

(wherein TPD is Equation 3.)

$$TPD = \frac{1}{N}\sum_{k=1}^{N} |Prof(A_k) - Prof(B_k)| \quad \text{(Equation 3)}$$

(wherein Prof(Ak) and Prof(Bk) are respective molecular orbital values belonging to RDM(k), and N is a total number of RDM.)

To obtain a MOD-Dscore value according to the present invention, first, two molecular orbitals to be compared for molecular orbital distributions are selected, and the molecular orbital distributions are calculated using quantum chemistry calculation in step i). A molecular orbital is defined as a mathematical function describing the wave-like behavior of an electron in a molecule. In the present invention, the two molecular orbitals to be compared for molecular orbital distribution may be two electron states of one molecule (for example, Neutral/HOMO and Neutral/LUMO for the same molecule), or the same or different electron states for two different molecules (for example, Neutral/HOMO of molecule A and Neutral/HOMO of molecule B, or Neutral/HOMO of molecule A and Anion/LUMO of molecule B). After two molecular orbitals for comparison of molecular orbital distributions are selected, quantum chemistry calculation for each molecular orbital is performed to give a molecular orbital distribution. Any calculation method that takes advantage of quantum chemistry may be employed to obtain molecular orbital distributions, without limitations. Preferable may be calculation through the distribution of the electron density function ($\psi^2$), which is a square of the orbital wave function ($\psi$), in each point determined in a molecular structure, or single point energy or geometry optimization calculation. In detail, the present inventors calculate molecular orbital distributions using the program MATERIALS STUDIO DMol3 (ACCELRYS) that uses the density functional theory (DFT).

Next, the calculation of MOD-Dscore values according to the present invention goes with ii) calculating structural properties of each molecular orbital by means of an RDM (radially discrete mesh) calculation method, followed by matching with the molecular orbital distributions computed in step i) to obtain molecular orbital distributions according to the structural properties.

The calculation of structural properties can be carried out using atomic coordinates of (x, y, z). This information should be combined with the molecular orbital distributions calculated according to the structural properties. The reason why the calculation of structural properties is needed is that the information of coordinates of molecular structures is just data spread over the molecule, but cannot provide any other valuable information. In the present invention, hence, the calculation of structural properties of a given molecule is RDM (radially discrete mesh) can be accomplished by creating an RDM (radially discrete mesh) starting from the center of the molecule, and then designating regions corresponding to RDMs to compute an RDM accounting for the entire molecular structure. This RDM represents meshes expanding at regular intervals in a radial direction from the center of the molecule. In calculating molecular structures by means of RDM, the intramolecular center (xc, yc, zc) is obtained as illustrated by the following Equations 1-1 to 1-3:

$$X_C = \frac{1}{N^{AT}}\sum_{k=1}^{N^{AT}} X_k \quad \text{(Equation 1-1)}$$

$$Y_C = \frac{1}{N^{AT}}\sum_{k=1}^{N^{AT}} Y_k \quad \text{(Equation 1-2)}$$

$$Z_C = \frac{1}{N^{AT}}\sum_{k=1}^{N^{AT}} Z_k \quad \text{(Equation 1-3)}$$

wherein $N^{AT}$ represents a total number of atomic coordinates constituting the molecule.

Using the RDM method described above, the molecular structure is subdivided, and the subdivided regions are matched with molecular orbital distributions.

Figure 2:
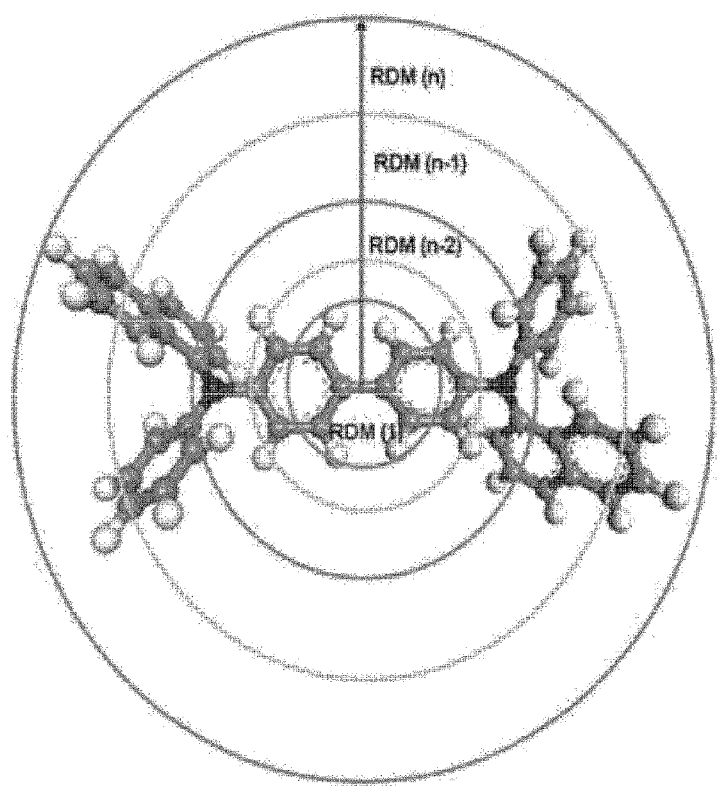
FIG. 2 is a schematic view illustrating RDM calculation.

RDM calculation can be further illustrated referring to FIG. 2. RDM is increased like RDM (1), RDM (2), . . . , and RDM (n) until all the atoms of the molecular structure are included. Here, RDM(1) is the most proximal to the center of the molecule while RDM(n) is the outermost RDM including the entire molecule therein. In the RDM calculation, n, the total number of RDMs, is set to be the same for the two molecular orbitals to be compared with each other. No special limitations are imparted to the n values; however, n preferably ranges from 50 to 300, and more preferably from 100 to 300. Molecular orbital distributions are calculated for each of the calculated RDMs. The molecular orbital information calculated with regard to the molecular structure is matched with molecular orbital information on structural properties converted into a total of n RDMs. The RDM information thus obtained is used for calculating a graph-based profile in step iii) as described later.

Subsequently, the calculation of MOD-Dscore values according to the present invention proceeds with step iii)

comparing in a profile process the molecular orbital distributions according to structural properties obtained through the two RDMs in step ii).

In the present invention, calculation of the two RDMs in step ii) can be used to account for the distribution of molecular orbitals with regard to each RDM. This is termed RDM-profile. In the present invention, a graph-based profile is created for the molecular orbital distributions matched through the RDM structure characterization of the two molecular orbitals, and used to calculate a profile deviation in the molecular orbital distribution of the graph, that is, a deviation of molecular orbital distribution in each RDM, with regard to the entire structure. The profile deviation in one RDM ranges from 0 to 1.0. When the profile deviation is 0 (zero), the two profiles are identical. A greater profile deviation means that the two profiles are more different. As such, profile comparison can indicate quantitative deviation of the molecular orbital distributions that are matched with regard to structures according to two molecular orbitals via each RDM. This can further embodied by obtaining the TPD (total profile deviation) of Equation 3, which represents the sum of all the RDMs:

$$TPD = \frac{1}{N}\sum_{k=1}^{N} |Prof(A_k) - Prof(B_k)| \quad \text{(Equation 3)}$$

(wherein Prof(Ak) and Prof(Bk) are molecular orbital values of respective RDM (k), and N is a total number of RDMs.)

Using the TPD value, MOD-Dscore by which a deviation between two molecular orbital distributions can be further quantitatively compared can be calculated according to the following Equation 2:

$$\text{MOD-}D\text{score} = 1.0 - TPD \quad \text{(Equation 2)}$$

Calculated values of MOD-Dscore are between 0.0 and 1.0. When two molecular orbital distributions are accurately identical, TPD has a value of 0.0, and thus MOD-Dscore is 1.0. Greater deviation between two molecular orbital distributions makes MOD-Dscore smaller than 1.0. As such, distribution deviation between two molecular orbitals can be quantitatively analyzed by MOD-Dscore.

As described above, a) A(1) belonging to a group of materials that have a specific-type molecular orbital is selected and then A(2) is selected if it has a MOD-Dscore value of p or less with regard to A(1), and b) A (1) and A(2), both determined in a), are incorporated as constituents A(m) into an R-MO library (Region specific-Molecular Orbital Library). The value p is not specifically limited so long as it is determined by the user. Preferable is 0.7≤p≤0.8 in which there is a sufficient deviation in molecular orbital distribution between A(1) and A(2).

In step c), A(3), a member selected from the group of the materials, is calculated for respective MOD-Dscore values with regard to plural materials already incorporated into the R-MO library (Region specific-Molecular Orbital Library), and then is incorporated as a constituent A(m) into the R-MO library (Region specific-Molecular Orbital Library) if the MOD-Dscore values are calculated to have a maximum of q or less and a minimum of r or less. No special limitations are imparted to the maximum value q so long as it is determined by the user. In order for the molecular orbital distributions to have similarity, 0.85≤q≤0.95 is preferable. Also, the minimum value r is not specifically limited so long as it is determined by the user. Preferable is 0.65≤r≤0.75 in order to provide a sufficient deviation between molecular orbital distributions.

In step d), step c) is repeated for all materials of the group to determine whether individual materials can be included within the R-MO library and thus to find the constituents A(m) of the R-MO library.

In step e), MOD-Dscore values of AX(1), one of the candidate materials AX(k) that are not incorporated into the R-MO library, are calculated with regard to all the constituents A(m) of the R-MO library obtained in step d), and if the MOD-Dscore values have a maximum of p' or greater, AX(1) is incorporated as an extended constituent Am(k') into the extended R-MO library (Extended-Region specific-Molecular Orbital Library) of the constituent A(m).

In step f), step e) is repeated for all candidate materials AX(k) to determine whether individual candidate materials can be included within the extended R-MO library, and thus to determine an extended material Am(k') of the extended R-MO library.

In the present invention, the concept of constructing the R-MO library (Region specific-Molecular Orbital Library) as in steps b) to d) is further explained with reference to FIGS. 3 to 5.

Figure 3:
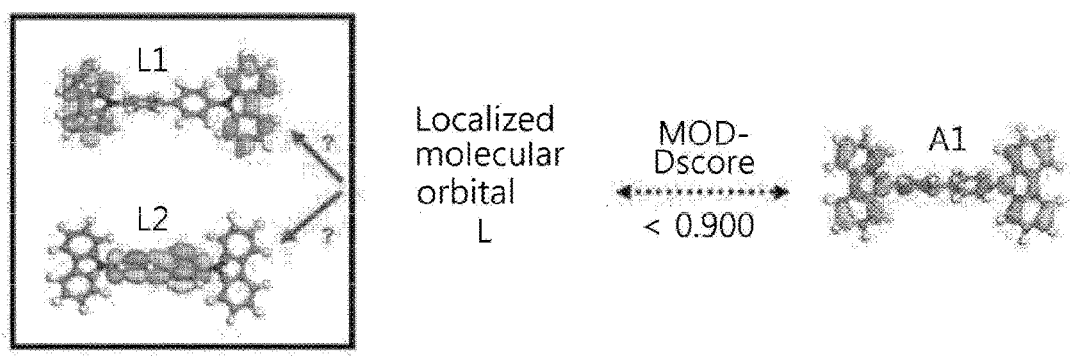
FIG. 3 is a diagram of the molecular orbital distribution of 4'-bis(N-carbazolyl)1,1'-biphenyl.

As shown in FIG. 3, when L1 and L2 the molecular orbitals of which are localized to (1) opposite ends and (2) the center, respectively, are calculated for MOD-Dscore with regard to A1 that has a molecular orbital evenly distributed over the entire structure thereof, both have a MOD-Dscore value less than 0.900, indicating that neither L1 nor L2 is similar in molecular orbital distribution to A1. From the MOD-Dscore values, however, it is difficult to determine accurate regions to which molecular orbitals of L1 and L2 are localized, which makes L1 and L2 different in property from A1 over the entire structure of which the molecular orbital is evenly distributed. To enhance quantitative estimation method of molecular orbital distributions using the MOD-Dscore, information on specific regions in which the molecular orbitals are localized should be obtained by searching for distribution regions of molecular orbitals. In this context, the present inventors suggest R-MO library (Region specific-Molecular Orbital Library) that plays a role as a reference in estimating regions that are different in molecular orbital distribution. R-MO library serves as a designated reference in estimating molecular orbital distributing regions between two materials to be compared.

R-MO library is a set of at least three materials with mutually exclusive molecular orbital distribution. Because the distribution regions are overlapped unless mutually exclusive, R-MO library cannot accurately estimate a region where molecular orbitals to be compared are present. Exclusive molecular orbital distribution relationship, which is a necessary condition for establishing the R-MO library, is elucidated in FIG. 4.

Figure 4:
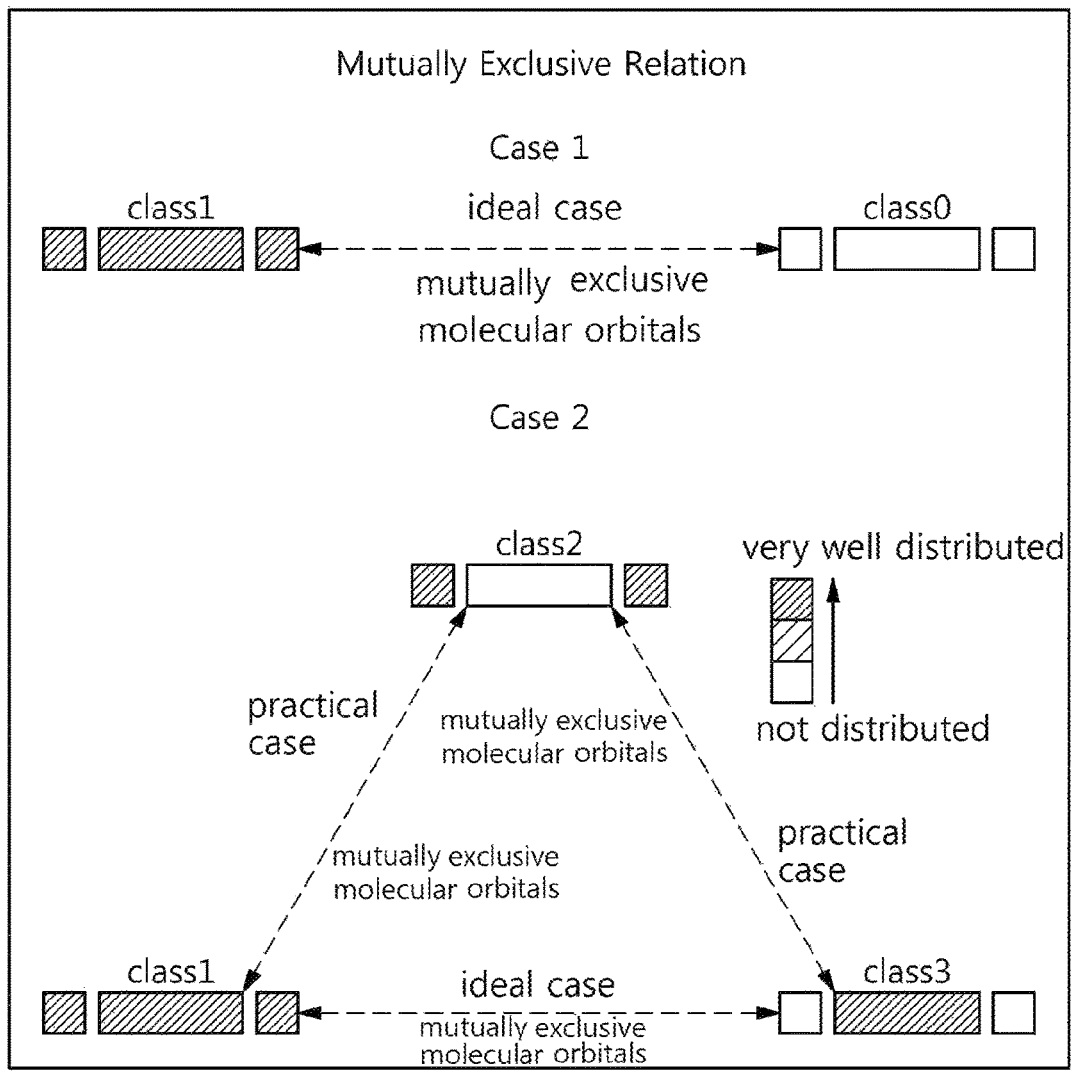
FIG. 4 is a schematic view illustrating molecular orbital distribution relationship of the R-MO library of the present invention.

In FIG. 4, rectangles represent specific regions within a molecular structure. Classes 0~3 indicate an entire molecular structure composed of three specific regions. Colors within the rectangles show levels of molecular orbital distributions. A darker color means a denser population of molecular orbitals. Thus, a white color indicates no distributions of molecular orbitals in the specific region.

Referring to case 1 of FIG. 4, class 1 shows even distributions of molecular orbitals in all the three specific regions. In contrast, there are no distributions of molecular orbitals in the three specific regions of class 0. However, no distribution of molecular orbitals over the entire regions of a molecule is actually impossible. Accordingly, class 0 represents an ideal orbital distribution mutually exclusive to class 1. There is therefore a need for definitions for mutually exclusive molecular orbital distributions.

Turning to case 2 of FIG. 4, (1) class 2 shows molecular orbitals distributed only in two opposite specific regions and (2) class 3 has a molecular orbital localized to the one central region while molecular orbitals are evenly distributed in all the three specific regions of class 1. Hence, classes 2 and 3 represent molecular orbital distribution properties that are not accounted for by class 1. In this regard, the relationship that different molecular orbital distributions represent respective, intrinsic properties is defined as mutually exclusive molecular orbital distribution. In addition, class 3 accounts for a property of the molecular orbital localized to one central region that cannot be represented by class 2. As such, R-MO library is composed of materials that have mutually molecular orbital distributions.

Figure 5:
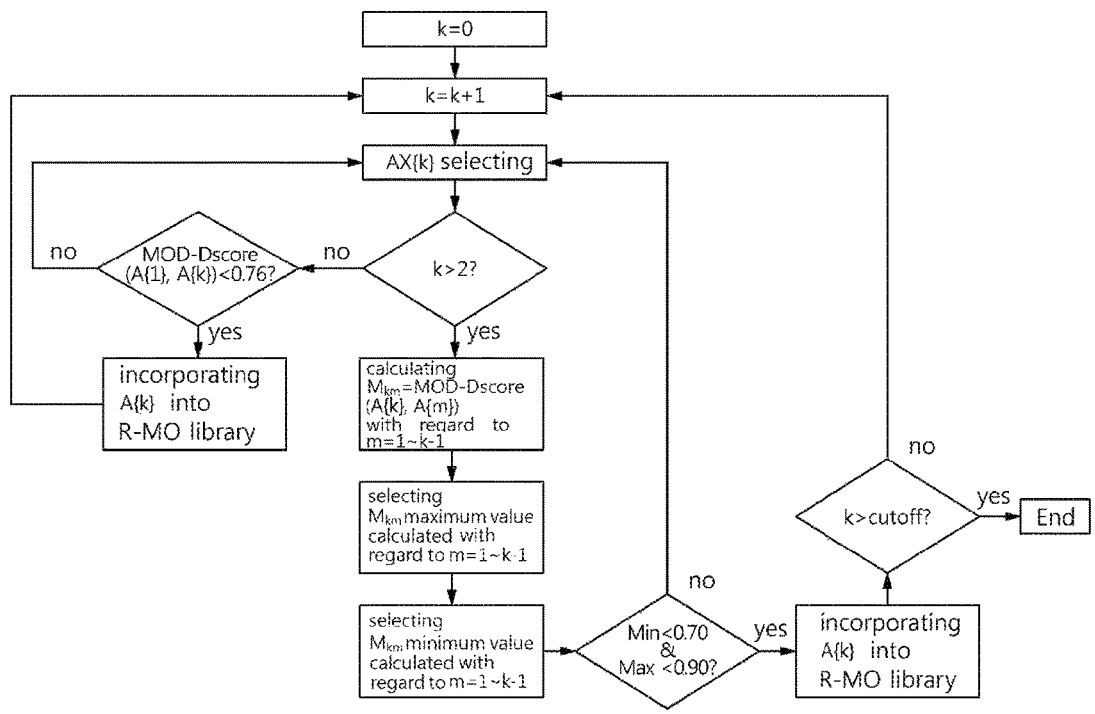
FIG. 5 is a flow chart illustrating the construction procedure of the R-MO library according to the present invention.

FIG. 5 is a flow chart illustrating the construction procedure of the R-MO library according to the present invention, as described in the following steps 1 to 4.

Step 1

An initial material with a certain molecular orbital is designated as A(1) (k=1). For example, any of classes 1~3 may be A(1).

Step 2

Selection is made of A(k), a material with a different molecular orbital (k=k+1). When k is 2 or less, MOD-Dscore is calculated to quantitatively explain molecular orbital distribution deviation between A(1) and A(k). At this time, if the MOD-Dscore value is smaller than 0.76, A(k) is incorporated into the R-MO library; otherwise, another A(k) is selected and calculated for MOD-Dscore value. This procedure is repeated until the MOD-Dscore value is found to be less than 0.76. By doing this, R-MO library can include A(1) and A(2), which have mutually exclusive molecular orbitals.

Step 3

In the case where two materials are included in the R-MO library, selection is made of A(k), a material with a molecular orbital property different from those of the two materials (k=k+1). This new A(k) is calculated for MOD-Dscore with regard to the preexisting materials. Of the calculated MOD-Dscore values, a maximum value (MAX) and a minimum value (MIN) are picked out. When MAX<0.90 and MIN<0.70, the selected A(k) is determined to have a molecular orbital exclusive to all the pre-existing materials of the R-MO library, and can be incorporated into the R-MO library.

Step 4

When k is smaller than a cutoff value, new A(k) is selected again and step 3 is repeated for the new material. When k is greater than a cutoff value, the construction of R-MO library may be completed because all materials with mutually exclusive molecular orbitals that constitute the R-MO library are selected. In the R-MO library, the cutoff value has a minimum of 3. That is to say, the R-MO library must include at least three materials with mutually exclusive molecular orbitals.

Consisting of three or more materials that have intrinsic, mutually exclusive molecular orbital distributions, the R-MO library constructed by the above-described procedure can exhibit various patterns of the molecular orbital that may be distributed in specific regions of the overall molecular structure. Accordingly, the R-MO library can be useful as a reference for estimating molecular orbital properties of certain materials in terms of orbital distribution.

Figure 8:
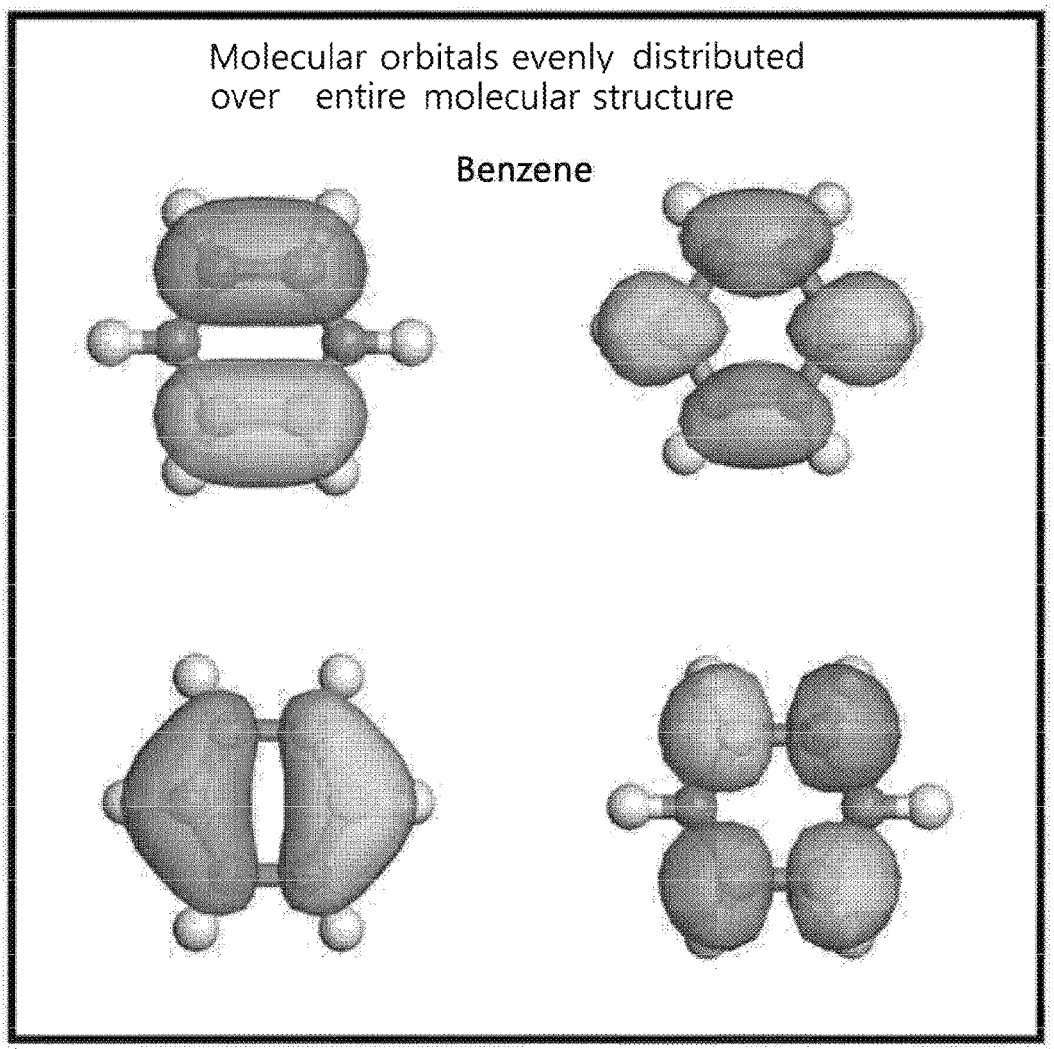
FIG. 8 is a diagram showing molecular orbital distributions of benzene.

However, molecular orbital distributions are very complex in pattern so that molecular orbital distributing region properties cannot be explained only by the molecular orbital distributions of one material. For instance, FIG. 8 is a diagram showing molecular orbital distributions of benzene, which is an aromatic hydrocarbon with the simplest structure, as calculated with regard to different charge states. In FIG. 8, regions where molecular orbitals are distributed appear yellow/green whereas the other regions represent absence of molecular orbitals. As can be seen, all the molecular orbitals are evenly distributed over the entire molecule. However, there are four molecular orbital distribution patterns that account for the same molecular orbital distributing region properties. As such, the intrinsic molecular orbital distributing region properties are too complex to be explained with a single molecular orbital distribution. That is, intrinsic molecular orbital distributing region properties are too variable to be accounted for only by the constituents of the R-MO library. For use as a reference that can cover molecular orbital distributing region properties, the R-MO library should exhibit intrinsic molecular orbital distribution properties in a variety of patterns.

For this necessity, the present inventors developed an extended version of the R-MO library that can cover a variety of distribution patterns.

To this end, an extended-region specific-molecular orbital library is constructed through steps e) to f), as described above, and its conception can be explained with reference to FIGS. 6 and 7.

Figure 6:
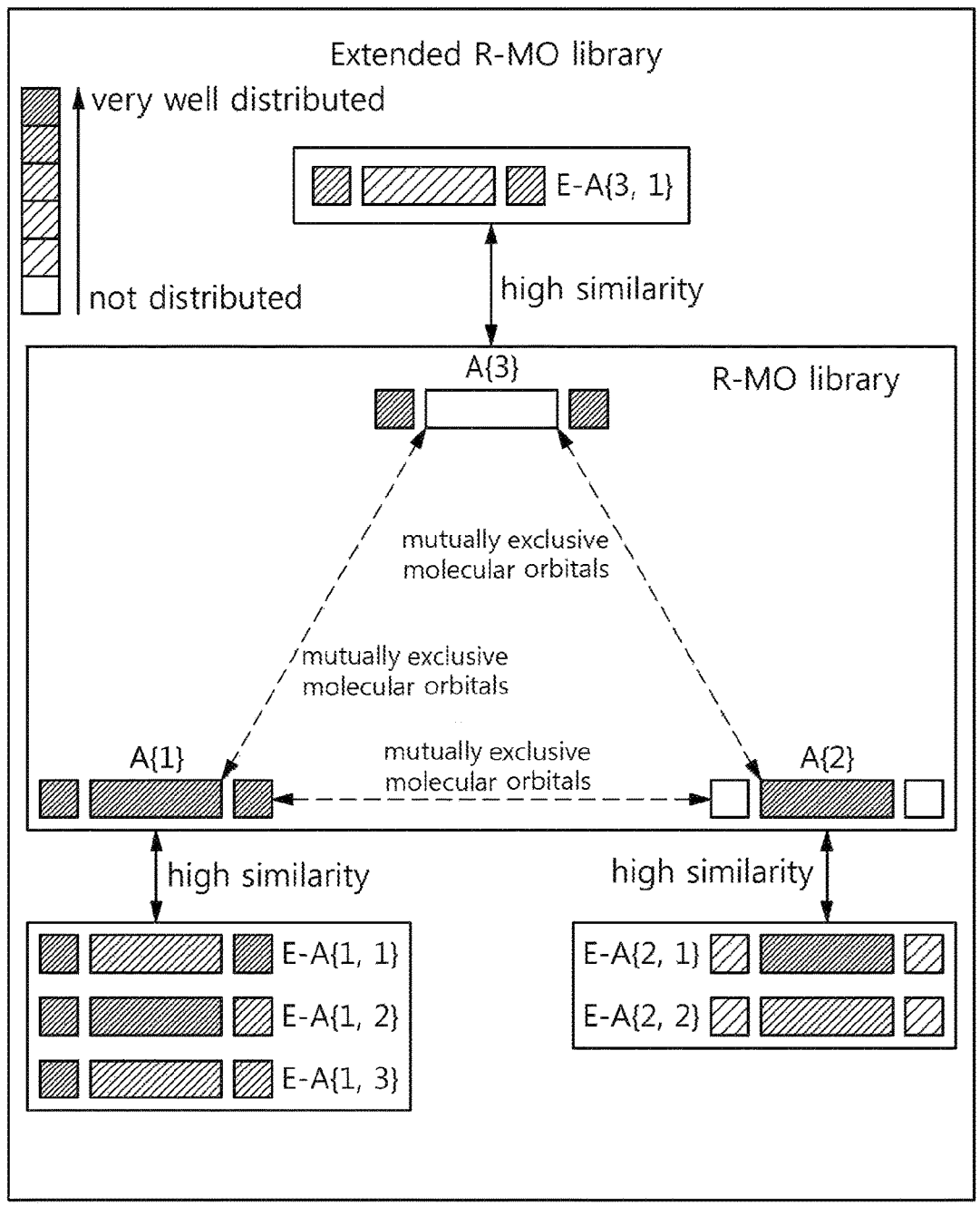
FIG. 6 is a schematic view illustrating molecular orbital distribution relationship of the extended R-MO library of the present invention.
Figure 7:
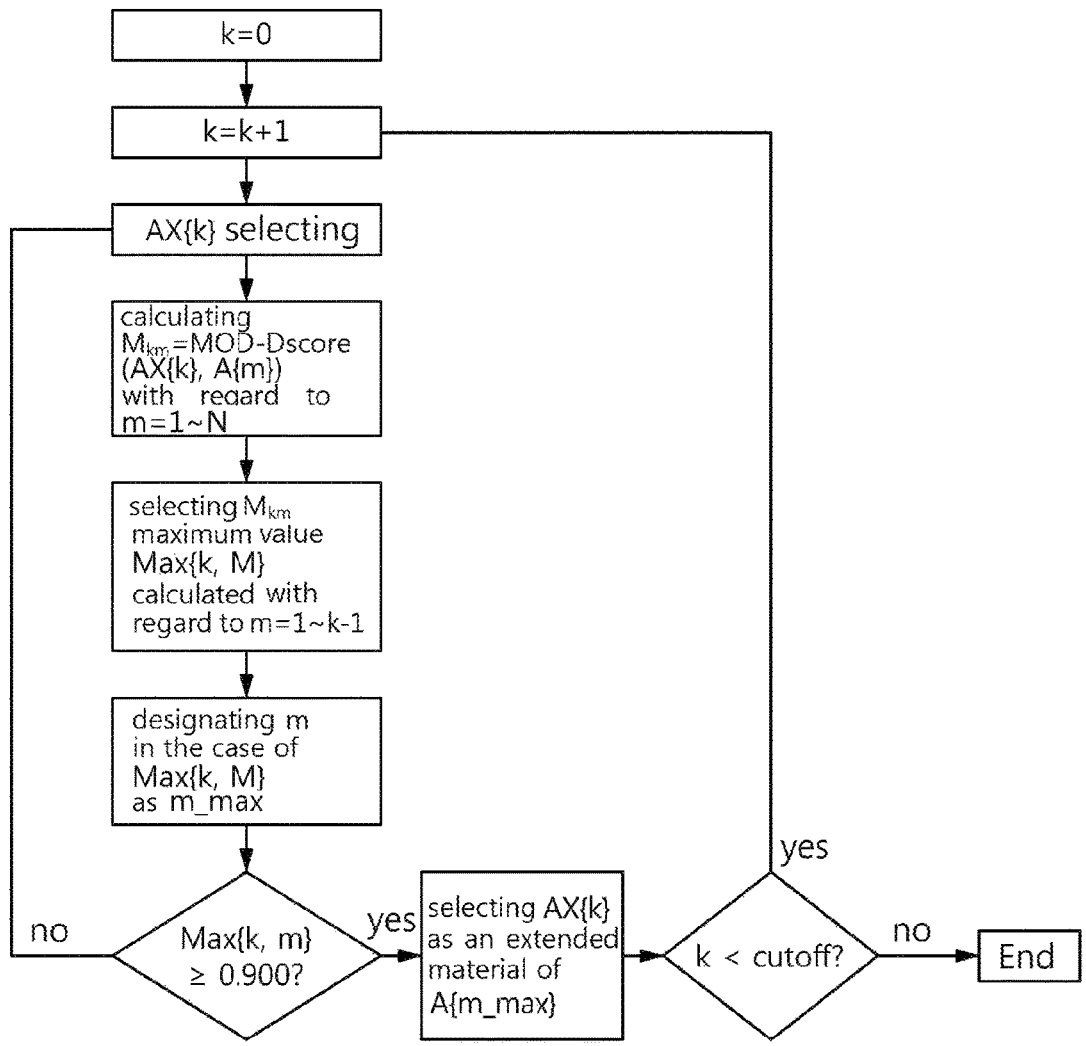
FIG. 7 is a flow chart illustrating the construction procedure of the extended R-MO library according to the present invention.

FIG. 6 is a schematic view illustrating the outline of the extended-region specific-molecular orbital library. In this schematic view, A{1}~A{3} are constituents of the R-MO library and rectangles represent specific regions within a molecular structure. Each of the three constituents is composed of three specific regions. In each specific region, a darker color means a denser population of molecular orbitals. Thus, a white color indicates no distributions of molecular orbitals in the specific region. Below, a detailed description is given of the concept.

Molecular orbital distributing region property that the R-MO library exhibits (1) A{1}: molecular orbital evenly distributed over three specific regions.

(2) A{2}: molecular orbital localized to the central region of the three specific regions.

(3) A{3}: molecular orbital localized to opposite end regions of the three specific regions.

An extended material that can represent various molecular orbital distribution patterns of the constituents of the R-MO library must be found. By way of example, a material the molecular orbital of which is well distributed in opposite two end specific regions, but is not distributed in the central region, like E-A{1,1}, can exhibit the molecular orbital distributing region property of A{1}, as well. Such a material that exhibits the same distribution region property as in A{1}, but in a different pattern is defined as an extended material (E-A{1,1}) for A{1}. A set of such extended materials can exhibit a variety of molecular orbital distributing region properties. Extended R-MO library includes extended materials that can exhibit various patterns of the molecular orbital distributing region properties represented by the constituents of the R-MO library. Extended materials of the extended R-MO library can be selected according to the constituent (A{m}, m=1~N) of the R-MO orbital library, as illustrated in the flow chart of FIG. 7, through the following calculation procedure.

Searching for Extended Material for Extended R-MO Library

Step 1-1)

A candidate AX{k} is calculated for molecular orbital. Any calculation method that takes advantage of quantum chemistry may be employed to obtain molecular orbital distributions.

Step 2-1)

Quantitative molecular orbital distribution deviation between the selected AX{k} and the constituents (A{m}, m=1~N) of the R-MO orbital library is calculated using MOD-Dscore (Mkm). N is a total number of the constituents included within the R-MO library.

Step 3-1)

Of the calculated Mkm, a maximum value (Max{k,m}) is sought. When m is given for the maximum value, it is designated m_max. Given Max{k,m} larger than 0.900, AX{k} is selected as an extended material (E-A{m_max,k}) for A{m_max}. When Max{k,m} is smaller than 0.900, a new AX{k} is selected and allowed to undergo steps 2 and 3. This procedure is repeated until AX{k} greater than 0.900 is found. When k is smaller than a cutoff value, set k=k+1 to select new AX{k} on which steps 2-1 and 3-1 are repeated; otherwise, the procedure is terminated.

By this way, extended materials for each constituent can be obtained, and used to construct the extended R-MO library, which can exhibit mutually exclusive molecular orbital distribution properties in a greater variety of patterns.

In addition, the present invention provides a quantitative analysis method of a molecular orbital distribution property using the extended R-MO library and the R-MO library.

The quantitative analysis method comprises:

a') calculating a target material T for MOD-Dscore values for any one of the constituents A(m) of the R-MO library and an extended material Am(k') to determine a minimum value MIN(m), and obtaining minimal values MIN(m) for all constituents A(m) of the extended R-MO library; and b') designating a greatest one of the minimal values MIN(m) obtained in step a') as M_MAX, and estimating the target material T as being similar to a constituent A(m) the minimum value MIN(m) of which is M_MAX if M_MAX is greater than p", wherein 0.84≤p"<1.0.

Figure 9:
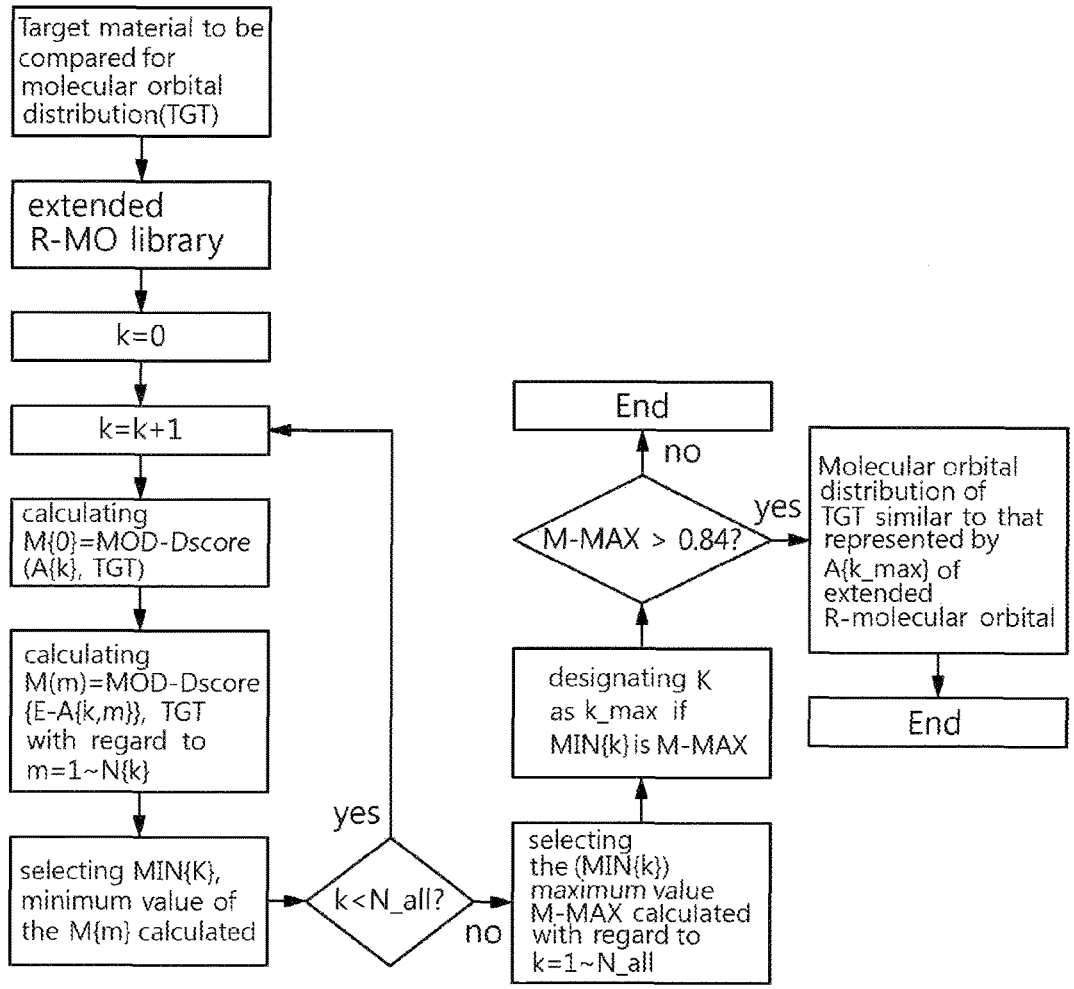
FIG. 9 is a flow chart illustrating the quantitative estimation of molecular orbital distributions properties according to the present invention.

The present inventors developed a MODREM (Molecular Orbital Distributing Region Estimation Method), a novel method for quantitatively estimating a molecular orbital distributing region using the extended R-MO library that is capable of exhibiting intrinsic molecular orbital distributing region properties in various patterns. The calculation algorithm of MODREM is explained in FIG. 9. With reference to FIG. 9, the MODREM will be in detail described as follows.

MODREM

Step 1-2)

A target material TGT is calculated for molecular orbital. Any calculation method that takes advantage of quantum chemistry may be employed to estimate molecular orbital distributing regions.

Step 2-2)

The extended R-MO library is used to estimate molecular orbital distributing regions. The extended R-MO library includes N_all constituents (A{k}, k=1~N_all), and corresponding extended materials (E-A{k,m}, m=1~N{k}, N{k} is a total number of extended materials for the kth constituent). Using MOD-Dscore, (1) molecular orbital distribution deviation (M{0}) between TGT and a constituent (A{k}), and (2) molecular orbital distribution deviation (M{m}, m=1,N{k}) between TGT and an extended material (E-A{k, m}) are calculated. From among the calculated values of N{k}+1 M{m}, minimum (MIN{k}) is selected. MIN{k} indicates a case where TGT is the most unlikely to resemble a molecular orbital distributing region property representative of A{k}.

Step 3-2)

Of the N_all MIN{k} finally calculated in step 2-2, a maximum value (M-MAX) is sought. When k is given for the maximum value, it is designated k_max. When M-MAX is larger than 0.84, the molecular orbital distributing region of TGT is estimated to be similar to a molecular orbital distributing region representative of A{k}. When M-MAX is smaller than 0.84, it is determined that the molecular orbital distributing region of TGT cannot be estimated using the extended R-MO library.

Also, the present invention addresses a system for constructing an extended R-MO library (Extended-Region specific-Molecular Orbital Library) using the constructing method of R-MO library (Region specific-Molecular Orbital Library).

The system comprises a) an initial setting module for selecting A(1) belonging to a group of materials that have a specific-type molecular orbital and then selecting A(2) if it has a MOD-Dscore value of p or less, as obtained by conducting the following steps i) to iii), with regard to A(1), and for incorporating A (1) and A(2) as constituents A(m) into an R-MO library (Region specific-Molecular Orbital Library): b) a constituent-determining module for calculating respective MOD-Dscore values of A(3), which is selected from the group of the materials, with regard to plural materials already incorporated into the R-MO library (Region specific-Molecular Orbital Library), for incorporating A(3) as a constituent A(m) into the R-MO library (Region specific-Molecular Orbital Library) if the MOD-Dscore values are calculated to have a maximum of q or less and a minimum of r or less, and for repeating the above procedure for all materials of the group to determine whether individual materials can be included within the R-MO library and thus to find the constituents A(m) of the R-MO library; and c) an extended material-determining module for calculating MOD-Dscore values of AX(1), one of the candidate materials AX(k) that are not incorporated into the R-MO library, with regard to all the constituents A(m) of the R-MO library, for incorporating AX(1) as an extended constituent Am(k') into the extended R-MO library (Extended-Region specific-Molecular Orbital Library) of the constituent A(m) if the MOD-Dscore values have a maximum of p' or greater; and for repeating the above procedure for all candidate materials AX(k) to determine whether individual candidate materials can be included within the extended R-MO library, wherein 0.7≤p≤0.8, 0.85≤q≤0.95, 0.65≤r≤0.75, and 0.90≤p'<1.0.

In the construction system, the two molecular orbitals to be compared for molecular orbital distribution may be two electron states of one molecule (for example, Neutral/HOMO and Neutral/LUMO for the same molecule), or the same or different electron states for two different molecules (for example, Neutral/HOMO of molecule A and Neutral/HOMO of molecule B, or Neutral/HOMO of molecule A and Anion/LUMO of molecule B).

Further, the present invention addresses a quantitative analysis system of a molecular orbital distribution property using the extended R-MO library and the R-MO library, comprising:

a') an initial setting module for calculating a target material T for MOD-Dscore values between any one of the constituents A(m) of the R-MO library and an extended material Am(k') corresponding to the constituent A(m) so as to determine a minimum value MIN(m), and for obtaining minimal values MIN(m) for all constituents A(m) of the extended R-MO library; and b') a similarity estimating module for designating a greatest one of the minimal values MIN(m) obtained in step a') as M_MAX, and for estimating the target material T as being similar to a constituent A(m) the minimum value MIN(m) of which is M_MAX if M_MAX is greater than p", wherein $0.84 \leq p" < 1.0$.

As used herein, the term "module" means a unit in which a certain function or action is processes, and may be embodied by hardware or software or a combination of hardware and software.

MODE FOR INVENTION

Reference will now be made in detail to various embodiments of the present invention, specific examples of which are illustrated in the accompanying drawings and described below, since the embodiments of the present invention can be variously modified in many different forms. While the present invention will be described in conjunction with exemplary embodiments thereof, it is to be understood that the present description is not intended to limit the present invention to those exemplary embodiments. On the contrary, the present invention is intended to cover not only the exemplary embodiments, but also various alternatives, modifications, equivalents and other embodiments that may be included within the spirit and scope of the present invention as defined by the appended claims.

EXAMPLES

Figure 10:
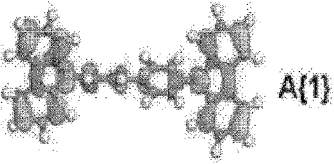
FIG. 10 shows an extended R-MO library constructed according to one exemplary embodiment of the present invention.

An extended R-MO library (Extended-Region specific-Molecular Orbital Library) according to the present invention was constructed as follows. FIG. 10 shows an extended R-MO library constructed for three specific regions. MODscore values calculated between constituents of the R-MO library and extended materials thereof are given below the extended materials. For calculating molecular orbital distributions, MATERIALS STUDIO DMol3 (ACCELRYS) was employed wherein n for RDM calculation was set to be 200.

Example 1: Construction of Extended R-MO Library

An extended R-MO library is composed of constituents of the R-MO library, and extended materials that can exhibit various patterns of the molecular orbital distributing region properties represented by the constituents. FIG. 10 shows an extended R-MO library including extended materials selected for the constituents of the R-MO library that have mutually exclusive molecular orbital distributing region properties with regard to three specific regions.

The molecular orbital distributing region property represented by the constituent A{1} is the even distribution of molecular orbital over the three specific regions. Investigation was made of extended materials corresponding to the constituent A{1}, using the method described above. Two materials were selected because they were found to have Max values of 0.985, and 0.971, respectively, with regard to A{1}. These newly selected, extended materials E-A{1,1} and E-A{1,2} can express various patterns of the molecular orbital distributing region property of A{1}. A{2} is responsible for the localization of molecular orbital to one central region while the corresponding extended material E-A{2,1} shows the same distributing region property, but in a different pattern. For A{3}, there are no selected, extended materials. Since the newly selected, extended materials express intrinsic molecular orbital distributing region properties in various patterns, the extended R-MO library can be more effectively used for estimating molecular orbital distributing regions than can the R-MO library.

Figure 11:
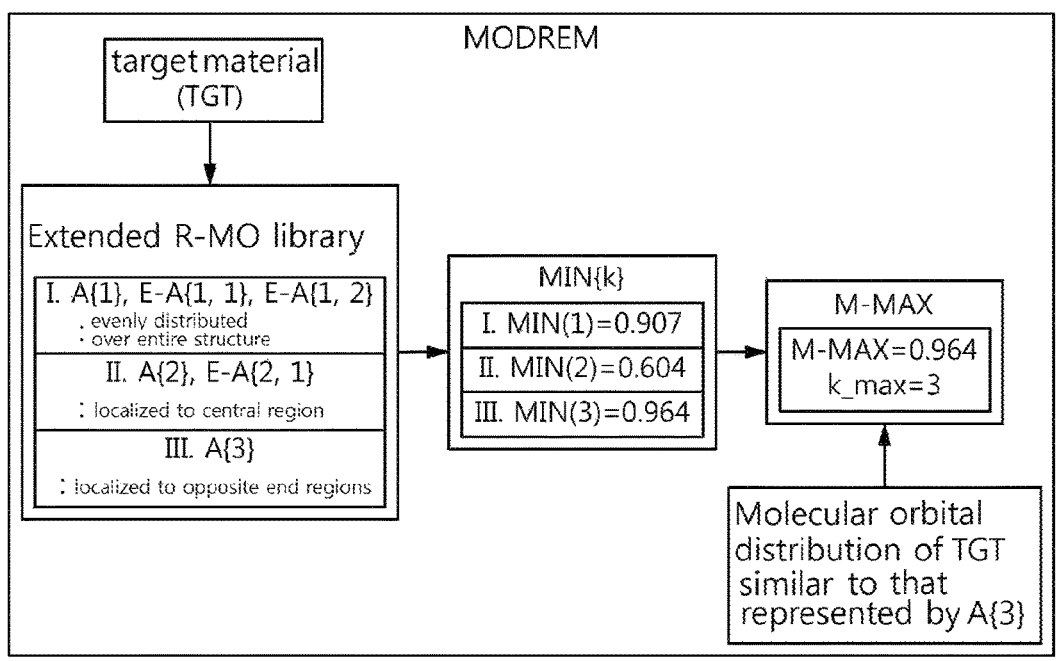
FIG. 11 is a schematic view illustrating the quantitative comparison of molecular orbital distributions constructed according to one exemplary embodiment of the present invention.

Example 2: Estimation Method of Molecular Orbital Distributing Region Using Extended R-MO Library: MODREM MODREM developed in the present invention was evaluated for ability to estimate molecular orbital distributing region properties. In this regard, the extended R-MO library composed of constituents showing mutually exclusive molecular orbital distribution properties with regard to the three specific regions, and corresponding, extended materials was used to apply MODREM to the estimation of molecular orbital distributing region properties of a target material TGT, as shown in FIG. 11.

Figure 12:
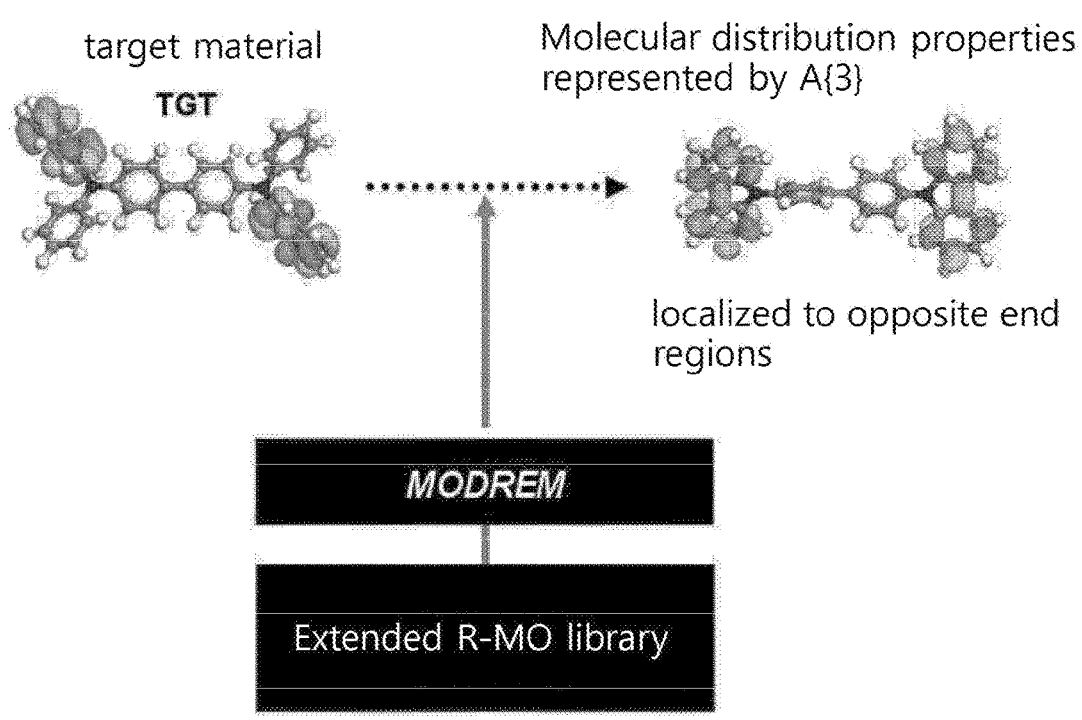
FIG. 12 shows comparison results of molecular orbital distribution properties, constructed in one exemplary embodiment of the present invention.

Using MODREM, calculation was made of MIN{k} with regard to molecular orbital distributing region properties represented by A{1}, A{2}, and A{3}, and finally of M-MAX. As a result, high similarity was found between TGT and the reference material since TGT was measured to have an M-MAX of 0.964 with regard to the molecular orbital distribution property represented by A{3}. That is, TGT was estimated to have molecular orbitals localized to opposite end regions. To confirm the estimation result of MODREM, the molecular orbital distributions of TGT are depicted in FIG. 12. Consistent with the estimation of MODREM, as shown in FIG. 12, TGT had molecular orbitals distributed only in opposite end specific regions, and thus exhibited the molecular orbital distributing region property of A{3}. Therefore, MODREM using the extended R-MO library was observed to accurate estimate molecular orbital distributing region properties.

The extended R-MO library in which materials with various molecular orbital distributing regions are exclusive to one another is developed from the conventional R-MO library the constituents of which are responsible only for their intrinsic molecular orbital distributing region properties, and can express the intrinsic molecular orbital distributing region properties in various patterns. Hence, the extended R-MO library can be used as a reference for more accurately estimating molecular orbital distributing regions. In addition, MODREM by which molecular orbital distributing regions can be quantitatively estimated using the extended R-MO library was practically applied and observed to accurately estimate molecular orbital distributing regions. Therefore, MODREM using the extended R-MO library is very useful in estimating molecular orbital distributions, and can develop the method of quantitatively estimating molecular orbital distributions to the estimation of molecular orbital distributing regions. Consequently, the present invention is expected to allow for the systemic utilization of information on molecular orbital distributions in developing materials.

Meanwhile, the present invention is not limited to the above-described embodiments and may be changed and modified, without departing from the gist of the present invention, and it should be understood that the technical spirit of such changes and modifications also belong to the scope of the accompanying claims.

The invention claimed is:

1. A method for quantitatively analyzing a molecular orbital distribution property, using an R-MO library (Region specific-Molecular Orbital Library) consisting of a constituent A(m) and an extended R-MO library consisting of extended material Am(k'), wherein the extended R-MO library is constructed by the following steps of a) to f):

a) selecting a molecular orbital A(1) belonging to a group of molecular orbitals that are different from each other, and then selecting a molecular orbital A(2) if it has a MOD-Dscore value of p or less, as obtained by conducting the following steps i) to iii), with regard to A(1):

i) selecting two molecular orbitals to be compared for molecular orbital distributions and computing molecular orbital distributions by quantum chemistry calculation, the two molecular orbitals to be compared for molecular orbital distribution are two electron states of one organic molecule, or the same or different electron states for two different organic molecules, ii) calculating structural properties of each molecular orbital carried out using atomic coordinates of (x, y, z) by means of an RDM (radially discrete mesh) calculation method carried out by creating meshes that are structured to expand at regular intervals in a radial direction, starting from a center of a molecule, and employs a total number (N) of 50 to 300 of RDM, followed by matching with the molecular orbital distributions computed in step i) to obtain molecular orbital distributions according to the structural properties from the RDM calculation method, iii) calculating MOD-Dscore (Molecular Orbital Distribution-Deviation Score) of following equation 2 by use of the molecular orbital distributions according to structural properties obtained in step ii);

b) incorporating A(1) and A(2), both determined in a), as a constituent A(m) into an R-MO library (Region specific-Molecular Orbital Library);

c) calculating respective MOD-Dscore values of a molecular orbital A(3), a member selected from the group of the materials, with regard to plural materials already incorporated into the R-MO library (Region specific-Molecular Orbital Library), and incorporating A(3) as a constituent into the R-MO library (Region specific-Molecular Orbital Library) if the MOD-Dscore values are calculated to have a maximum of q or less and a minimum of r or less;

d) repeating step c) for all materials of the group to determine whether individual materials can be included within the R-MO library and thus to find a constituent A(m) of the R-MO library;

e) calculating MOD-Dscore values of AX(1), which is one of the candidate molecular orbital AX(k) that is not incorporated into the R-MO library, with regard to all the constituents A(m) of the R-MO library obtained in step d), and incorporating AX(1) as an extended constituent Am(k') into an extended R-MO library (Extended-Region specific-Molecular Orbital Library) of the constituent A(m) if the MOD-Dscore values have a maximum of p' or greater; and f) repeating step e) for all candidate molecular orbital AX(k) to determine whether individual candidate materials can be included within the extended R-MO library, wherein $0.7 \le p \le 0.8$, $0.85 \le q \le 0.95$, $0.65 \le r \le 0.75$, and $0.90 \le p' < 1.0$, $$\text{MOD-}D\text{score} = 1.0 - TPD \quad \text{(Equation 2)}$$

wherein TPD (total profile deviation) is represented by Equation 3, $$TPD = \frac{1}{N}\sum_{k=1}^{N} |Prof(A_k) - Prof(B_k)| \quad \text{(Equation 3)}$$

wherein $Prof(A_k)$ and $Prof(B_k)$ are respective molecular orbital values belonging to RDM(k), and N is a total number of RDM, and wherein the method for quantitatively analyzing a molecular orbital distribution property comprises:

a') calculating a target material T for the MOD-Dscore values for any one of the constituents A(m) of the R-MO library and an extended material Am(k') to determine a minimum value MIN(m), and obtaining minimal values MIN(m) for all constituents A(m) of the extended R-MO library; and b') designating a greatest one of the minimal values MIN(m) obtained in step a') as M_MAX, and estimating the target material T as being similar to the constituent A(m), the minimum value MIN(m) of which is M_MAX if M_MAX is greater than p", wherein $0.84 \le p" < 1.0$.

2. The method of claim 1, wherein the quantum chemistry calculation of step i) is conducted using an electron density function ($\psi^2$) in each point determined in a molecular structure, the electron density function being a square of an orbital wave function ($\psi$).

3. The method of claim 1, wherein the quantum chemistry calculation of step i) is conducted using single point energy or geometry optimization calculation.

* * * * *